(12) United States Patent
Hemstad

(10) Patent No.: US 10,328,164 B2
(45) Date of Patent: Jun. 25, 2019

(54) RADIOPHARMACEUTICAL PRODUCTS

(75) Inventor: Stig Hemstad, Oslo (NO)

(73) Assignee: GE HEALTHCARE LIMITED, Buckinghamshire (GB)

(*) Notice: Subject to any disclaimer, the term of this patent is extended or adjusted under 35 U.S.C. 154(b) by 996 days.

(21) Appl. No.: 12/305,977

(22) PCT Filed: Jun. 21, 2007

(86) PCT No.: PCT/GB2007/002302
§ 371 (c)(1),
(2), (4) Date: Dec. 22, 2008

(87) PCT Pub. No.: WO2007/148088
PCT Pub. Date: Dec. 27, 2007

(65) Prior Publication Data
US 2009/0297442 A1 Dec. 3, 2009

Related U.S. Application Data

(60) Provisional application No. 60/832,190, filed on Jul. 20, 2006.

(30) Foreign Application Priority Data

Jun. 21, 2006 (GB) .................................. 0612333.5

(51) Int. Cl.
*A61K 51/00* (2006.01)
*A61M 36/14* (2006.01)
*A61K 51/12* (2006.01)

(52) U.S. Cl.
CPC ................................ *A61K 51/1286* (2013.01)

(58) Field of Classification Search
CPC .................................................. A61K 51/1286
USPC ....................................................... 424/1.61
See application file for complete search history.

(56) References Cited

U.S. PATENT DOCUMENTS

| | | | |
|---|---|---|---|
| 3,811,591 A | | 5/1974 | Novitch |
| 5,045,302 A | * | 9/1991 | Kelly et al. ............... 534/14 |
| 6,162,648 A | | 12/2000 | Maloney et al. |
| 6,713,042 B2 | * | 3/2004 | Liu ......................... 424/1.65 |
| 6,814,319 B2 | * | 11/2004 | Haskell ...................... 241/21 |
| 6,818,178 B2 | * | 11/2004 | Kohl ........................ A61L 2/07 |
| | | | 134/102.3 |
| 7,011,816 B2 | | 3/2006 | Griffiths et al. |
| 7,052,672 B2 | * | 5/2006 | Forster et al. ........... 424/1.65 |
| 7,504,646 B2 | * | 3/2009 | Balestracci et al. ..... 250/507.1 |
| 2002/0058647 A1 | * | 5/2002 | Handreck et al. ........... 514/102 |
| 2002/0119200 A1 | | 8/2002 | Haskell |
| 2003/0148030 A1 | * | 8/2003 | Vernon et al. ........... 427/255.28 |
| 2004/0057899 A1 | * | 3/2004 | Forster et al. ........... 424/1.11 |
| 2006/0275215 A1 | * | 12/2006 | Hiscock et al. ........... 424/1.69 |
| 2007/0031490 A1 | * | 2/2007 | Loebenberg ......... A61K 9/0007 |
| | | | 424/466 |
| 2007/0166187 A1 | * | 7/2007 | Song et al. ................. 422/40 |

FOREIGN PATENT DOCUMENTS

| | | |
|---|---|---|
| EP | 0162455 | 1/1989 |
| EP | 0294127 | 11/1994 |
| JP | 2006-257041 | 9/2006 |
| WO | 03/059397 | 7/2003 |
| WO | 2004/019861 | 3/2004 |
| WO | WO 2004/032936 | 4/2004 |
| WO | WO 2005053752 A2 * | 6/2005 |
| WO | 2006/026603 | 3/2006 |
| WO | 2006/044908 | 4/2006 |
| WO | WO 2006064175 A1 * | 6/2006 |
| WO | 2007042781 A2 | 4/2007 |

OTHER PUBLICATIONS

Bradley et al. Polyhedron, 1988, 7, 14, 1289-1298.*
Cannan et al. JACS, 1938, 60, 2314-2320.*
Murray, et.al. "Technetium-99-mtetrofosmin: retention of nitrogen atmosphere in kit vial as a cause of poor quality material" Nuclear Medicine Communications, vol. 21, 2000, pp. 845-849.
Reischl, G., et.al. "Highly efficient automated synthesis of [11C]choline for multidose utilization" Applied Radiation and Isotopes, vol. 60, 2004, pp. 835-838.
PCT/GB2007/002302 Int'l Search Report/Written Opinion dated Apr. 2008.
Great Britain 0612333.5 Search Report dated Oct. 2006.
Satyamurthy, N., et al., "Electronic Generators for the Production of Positron-Emitter Labeled Radiopharmaceuticals: Where Would PET Be Without Them?", Clinical Positron Imaging, 2(5), (1999) 233-253.
Office Action From Russian Patent Office dated Feb. 21, 2011 Issued on Corresponding Application No. 2008151890.
Saito, et.al, Polymer 1992 p. 770-773.
Griffiths, The Journal of Nuclear Medicine, vol. 45, No. 1, Jan. 2004 pp. 30-39.
Leece, Applied Radiation and Isotopes, 80, 2013, p. 99-102.
Summary of Product Characteristics: Cardiolote Mar. 2002.
Renewal of Marketing Authorisation: Leukoscan—Sulesomab Sep. 30, 2002.
Renewal of Marketing Authorisation: Datscan—Ioflupane Nov. 7, 2005.
Renewal of Marketing Authorisation: Ytracis.
Renewal of Marketing: Octreoscan.
Extract from Ullmann's Encyclopedia of Industrial Chemistry, fifth edition, Volume. A11, Fibers, synthetic inorganic to Formaldehyde, 1988.
"The West Company brochure for Daikyo Flurotec® Closures", dated Aug. 15, 1992.
Gebhardt, U. et al., "Particulate Contamination from Siliconized Rubber Closures for Freeze Drying", PDA Journal of Pharmaceutical Science and Technology 50 pp. 24-29, 1996.
West Pharmaceutical Services—Barrier Film web page, Oct. 30, 2003.

(Continued)

*Primary Examiner* — Michael G. Hartley
*Assistant Examiner* — Sean R Donohue
(74) *Attorney, Agent, or Firm* — Arent Fox LLP

(57) ABSTRACT

The present invention relates to improved radiopharmaceutical compositions in sealed containers, where the container closure has an ETFE (ethylene-tetrafluoroethylene copolymer) coating. Also disclosed are kits for radiopharmaceutical preparation using the sealed containers, as well as methods of preparation of radiopharmaceuticals using the sealed containers.

8 Claims, 2 Drawing Sheets

(56) References Cited

OTHER PUBLICATIONS

Daikyo Seiko—Flurotec web page, 2003.
Myoview™ prescribing information, Amersham Health/Medi-Physics, Inc., Mar. 2005.
The Source article from West Pharmaceutical Services, Issue 3, Nov. 2005.
Ebnesajjad, Sina et al., "Fluoropolymers applications in chemical processing industries, The Definitive User's Guide and Databook", William Andrew Publishing, pp. 51-52, 100-101' 107-110, 2005.
Saha, Gopal B., Extract from "Basics of PET Imaging", Springer, 2005.
GB Application No. GB0612333.5 filed on Jun. 21, 2006.
U.S. Appl. No. 60/832,190, filed Jul. 20, 2006.
Formulation Characteristics of 411 0/40 grey, West Delivering Innovative Solutions, Aug. 22, 2008.
Adelphi Healthcare Packaging, packaging stock list "Adelphi Healthcare Packaging—Stock Rubber Stoppers". Retrieved from the internet on Dec. 10, 2012.
Adelphi Healthcare Packaging, brochure titled "adding our personal touch". Retrieved from the internet on Dec. 10, 2012.
Declaration of Dr. Richard R. Cesati III dated Dec. 13, 2012 and annexes A to C.
DuPont Tefzel—Properties handbook, Fluoropolymer resin, The Miracles of Science Mar. 17, 2006.
Screenshot of Wayback Machine archive page dated Nov. 23, 2011 showing date for DuPont Tefzel reference.
In-Pharma Technologist article 2002.
Notice of opposition to corresponding European patent EP2029178 filed by Bergenstrahle & Lindvall AB on Dec. 13, 2013.
Notice of opposition to corresponding European patent EP2029178 filed by Lantheus Medical Imaging, Inc on Dec. 14, 2013.
Chinese Office Action Received for Chinese Patent Application 201510604306.2 dated Oct. 16, 2017, 20 Pages (9 pages Official Copy + 11 Pages English Translation).
Norway Office Action and Search Report corresponding to NO Application No. 20090210, dated Aug. 27, 2018 (with English Translated Office Action).

\* cited by examiner

Figure 1: Sealing Area of Flurotec™ Closure
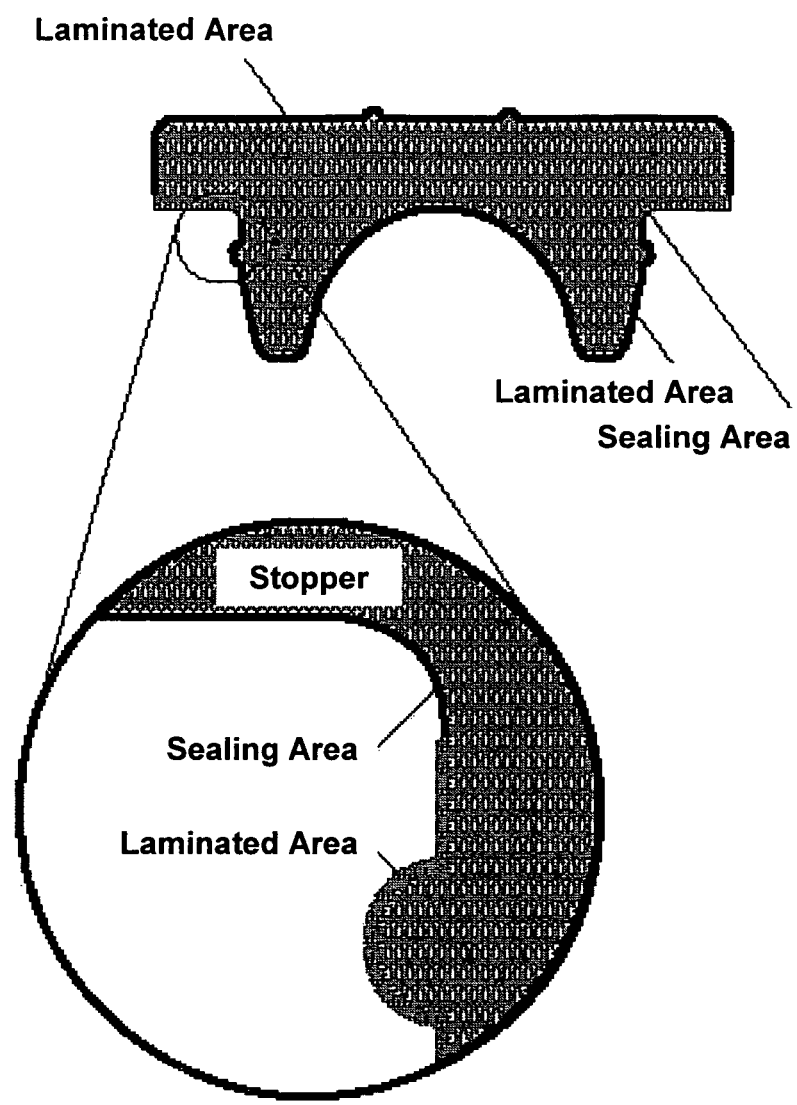

Figure 2: Oxygen Headspace (in µL) of Pre-treated Closures of Example 5.
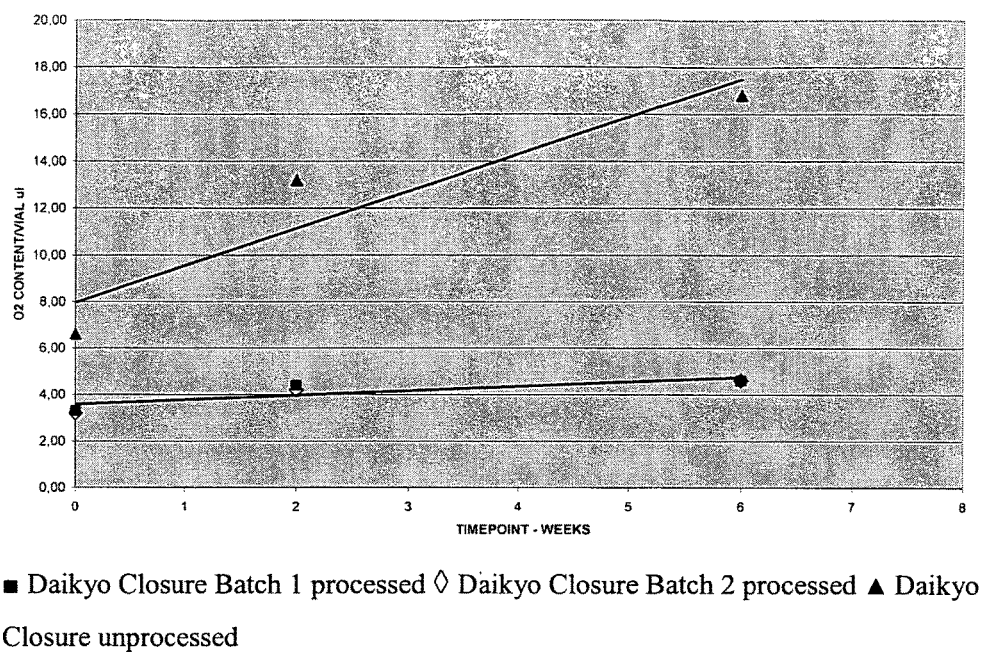
■ Daikyo Closure Batch 1 processed ◊ Daikyo Closure Batch 2 processed ▲ Daikyo Closure unprocessed

RADIOPHARMACEUTICAL PRODUCTS

This application is a filing under 35 U.S.C. 371 of international application number PCT/GB2007/002302, filed Jun. 21, 2007, which claims priority to application number 0612333.5 filed Jun. 21, 2006, in Great Britain and application No. 60/832,190 filed Jul. 20, 2006 in the United States the entire disclosure of which is hereby incorporated by reference.

FIELD OF THE INVENTION

The present invention relates to improved radiopharmaceutical compositions in sealed containers, where the container closure has an ETFE (ethylene-tetrafluoroethylene copolymer) coating.

BACKGROUND TO THE INVENTION

It is known to provide radiopharmaceutical compositions in sealed containers which are fitted with pharmaceutical grade closures, thus permitting the withdrawal of one or more doses for patient administration from the container.

A huge variety of pharmaceutical grade closures are commercially available, in a wide range of materials, shapes and sizes, together with optional coatings comprising a range of materials [Hencken & Petersen, Pharm. Ind., 65(9a), 966-976 (2003)]. The selection of a particular class or type of closure with the optimum characteristics for a given type of product is therefore not straightforward.

U.S. Pat. No. 6,162,648 provides a method of purification of the radioisotope $^{111}$In for radiopharmaceutical use. U.S. Pat. No. 6,162,648 teaches (Column 2) that, when a closure-sealed vial is used for the $^{111}$In, a rubber stopper coated with PTFE (polytetrafluoroethylene) on the surfaces facing the solution is beneficial. The coating is said to prevent leaching of impurities from the rubber of the stopper into the radioactive solution. Preferred stoppers of U.S. Pat. No. 6,162,648 are made of vinyl butyl rubber with the coating preferably the Teflon™ brand of PTFE.

WO 2006/026603 discloses improved containers for radioisotope generators, especially radiopharmaceutical generators for the positron-emitting radioisotope $^{82}$Rb. An improved crimped-on stopper seal is described, which is made of a material resistant to or tolerant of radiation and which can withstand pressure without ballooning. A range of coated and uncoated stopper materials was studied for suitability, especially with respect to resistance to radiation doses comparable to those prevailing during the working lifetime of the generator. Three uncoated elastomeric stopper materials were identified as preferred: 4588/40 isoprene/chlorobutyl; 6720 bromobutyl and 140/0 chlorobutyl. The most preferred stopper material was said to be 4588/40 isoprene/chlorobutyl.

Dalkyo Seiko's technical information sheet on their Fluorotec™-coated stoppers (D21 Formulation), where Fluorotec™ is Dalkyo's brand of ETFE, lists various advantages for the laminated fluoro resin film closure:

(i) an effective barrier to drug-closure interaction, preventing deterioration of the drug product and thus enhancing stability, maintaining potency and extending shelf-life. Applicable for drugs packaged at very low or very high pH;

(ii) eliminates endogenous particles of rubber stoppers;

(iii) excellent resistance to drug-closure adsorption, thus compatible with low dose and low volume fill drugs;

(iv) laminated coating provides excellent lubricity, eliminating closure sticking or clumping problems during batch manufacture and eliminating the need for silicone treatments of the closure.

The Dalkyo Seiko catalogue suggests that the closures are useful for freeze-dried preparations, powdered preparations, liquid preparations and transfusion preparations. The Catalogue states that the closures should not be exposed to direct sunlight or intense ultraviolet rays, and are supplied non-sterile (ie. for pharmaceutical applications must be sterilised before use). Both the technical information sheet and Catalogue are silent on radiopharmaceutical applications and/or whether the closures are radioresistant (ie. can withstand radiation dose).

THE PRESENT INVENTION

The present invention provides improved radiopharmaceutical product container compositions in sealed containers, where the container closure has an ETFE (ethylene-tetrafluoroethylene copolymer) coating. The selection of these closures from the wide range of pharmaceutical grade closures available has been found to have particular advantages for radiopharmaceutical preparations.

Radiopharmaceuticals are typically present at extremely low (typically micromolar, nanomolar or lower) chemical concentrations. The chemical content is thus much lower than even the lowest drug formulation. Consequently, even low levels of leached impurities (eg. metal ions or organics) from the closure, can have a significant effect on the radiochemical purity. This could occur eg. by leached non-radioactive metal ions displacing the radiometal from radiometal complexes and thus increasing the levels of free radiometal impurity. Such free radiometal could then generate further radioactive impurities by undergoing e.g. redox reactions, or complexation with other available ligands. Similarly, ingress of tiny levels of oxygen into the headspace gas can have a disproportionately large effect due to the extremely low chemical concentrations of radiopharmaceutical present. The sealed containers with ETFE-coated closures of the present invention have been shown to be particularly suitable for radiopharmaceuticals. The present invention also shows that the containers of the invention are also advantageous for use with kits for the preparation of radiopharmaceuticals, particularly those having lyophilised precursors.

DETAILED DESCRIPTION OF THE INVENTION

In a first aspect, the present invention provides an imaging agent product which comprises a radiopharmaceutical composition supplied within a sealed container, wherein:

(i) said radiopharmaceutical composition comprises a radioisotope suitable for medical imaging provided in a biocompatible carrier, in a form suitable for mammalian administration;

(ii) said sealed container is provided with a closure suitable for puncturing with a hypodermic needle whilst maintaining seal integrity, and said closure is coated on those of its surface(s) which are in contact with the container contents with a coating comprising ethylene-tetrafluoroethylene copolymer (ETFE) or modified versions thereof.

The term "radiopharmaceutical" has its conventional meaning, ie. a radioactive pharmaceutical or compound in a form suitable for administration to the mammalian, especially human, body. Radiopharmaceuticals are used for diagnostic imaging or radiotherapy. The radiopharmaceuticals of the present invention are preferably used for diagnostic imaging.

The sealed containers of the present invention are pharmaceutical grade containers suitable for the storage and shipment of radiopharmaceuticals whilst maintaining sterile integrity. Such containers may contain single or multiple patient doses of the radiopharmaceutical composition. Preferred multiple dose containers comprise a single bulk vial (e.g. of 10 to 30 cm$^3$ volume) which contains several patient doses, whereby single patient doses can thus be withdrawn into clinical grade syringes at various time intervals during the viable lifetime of the preparation to suit the clinical situation. A preferred such container is a pharmaceutical grade vial. The vial is suitably made of a pharmaceutical grade material, typically glass or plastic, preferably glass. The glass of the container may optionally be coated to suppress leachables from the glass, as is known in the art. A preferred such coating is silica ($SiO_2$). Pharmaceutical grade glass vials which are coated with high purity silica are commercially available from Schott Glaswerke AG, and other suppliers.

The radiopharmaceutical compositions of the present invention are in sterile form suitable for mammalian, especially human, administration. The compositions may thus be prepared under aseptic manufacture conditions to give the desired sterile product. The radiopharmaceutical compositions may also be prepared under non-sterile conditions, followed by terminal sterilisation using e.g. gamma-irradiation, autoclaving, dry heat or chemical treatment (e.g. with ethylene oxide). Autoclaving is used in conventional pharmaceutical practice, but the closures of the present invention are preferably sterilised by gamma irradiation. That is because autoclaving leaves traces of residual moisture within the closure, and some radiopharmaceuticals are moisture-sensitive. Myoview™ ($^{99m}$Tc-tetrofosmin) is an important example where it is strongly preferred to suppress the moisture content of the closure.

The headspace gas above the radiopharmaceutical composition in the sealed container is suitably a chemically unreactive gas. By the term "chemically unreactive gas" is meant a gas which would be used in chemistry to provide an "inert atmosphere" as is known in the art. Such a gas does not undergo facile oxidation or reduction reactions (eg. as would oxygen and hydrogen respectively), or other chemical reactions with organic compounds (as would eg. chlorine), and is hence compatible with a wide range of synthetic compounds without reacting with the synthetic compound, even on prolonged storage over many hours or even weeks in contact with the gas. Suitable such gases include nitrogen or the inert gases such as helium or argon. Preferably the chemically unreactive gas is nitrogen or argon. Pharmaceutical grade chemically unreactive gases are commercially available.

The "radioisotope suitable for medical imaging" of the radiopharmaceutical of the present invention may be present in a variety of chemical forms. One possibility is that the radioisotope is in ionic form dissolved in the biocompatible carrier. Examples of this are $^{201}$Tl as thallous chloride, $^{67}$Ga citrate or sodium $^{123}$I-iodide. Radioisotopes which are radiometals may also be present in covalent form as metal complexes of ligands, as is described below. The radiopharmaceutical may also comprise a biological targeting molecule which is labelled with the radioisotope. The term "labelled with" means that either a functional group comprises the radioisotope, or the radioisotope is attached as an additional species. When a functional group comprises the radioisotope, this means that the radioisotope forms part of the chemical structure, and is a radioactive isotope present at a level significantly above the natural abundance level of said isotope. Such elevated or enriched levels of isotope are suitably at least 5 times, preferably at least 10 times, most preferably at least 20 times; and ideally either at least 50 times the natural abundance level of the isotope in question, or present at a level where the level of enrichment of the isotope in question is 90 to 100%. Examples of such functional groups include $CH_3$ groups with elevated levels of $^{11}$C, and fluoroalkyl groups with elevated levels of $^{18}$F, such that the imaging radioisotope is the isotopically labelled $^{11}$C or $^{18}$F atom within the chemical structure. The radioisotopes $^3$H and $^{14}$C are not suitable for radiopharmaceutical imaging.

By the term "biological targeting moiety" is meant: 3-100 mer peptides or peptide analogues which may be linear peptides or cyclic peptides or combinations thereof; monoclonal antibodies or fragments thereof; or enzyme substrates or inhibitors; synthetic receptor-binding compounds; oligonucleotides, or oligo-DNA or oligo-RNA fragments. The biological targeting moiety may be of synthetic or natural origin, but is preferably synthetic. Preferred biological targeting moieties are 3-20 mer peptides, which may be of synthetic or natural origin, but are preferably synthetic. By the term "cyclic peptide" is meant a sequence of 5 to 15 amino acids in which the two terminal amino acids are bonded together by a covalent bond which may be a peptide or disulphide bond or a synthetic non-peptide bond such as a thioether, phosphodiester, disiloxane or urethane bond.

By the term "amino acid" is meant an L- or D-amino acid, amino acid analogue or amino acid mimetic which may be naturally occurring or of purely synthetic origin, and may be optically pure, i.e. a single enantiomer and hence chiral, or a mixture of enantiomers. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)].

Suitable peptides for use in the present invention include:
somatostatin, octreotide and analogues,
peptides which bind to the ST receptor, where ST refers to the heat-stable toxin produced by *E. coli* and other micro-organisms;
laminin fragments eg. YIGSR, PDSGR, IKVAV, LRE and KCQAGTFALRGDPQG,
N-formyl peptides for targeting sites of leucocyte accumulation,
Platelet factor 4 (PF4) and fragments thereof,
RGD-containing peptides, which may eg. target angiogenesis [R. Pasqualini et al., Nat. Biotechnol., 15(6): 542-6 (1997)]; [E. Ruoslahti, Kidney Int., 51(5):1413-7 (1997)].
peptide fragments of $α_2$-antiplasmin, fibronectin or beta-casein, fibrinogen or thrombospondin. The amino acid sequences of $α_2$-antiplasmin, fibronectin, beta-casein, fibrinogen and thrombospondin can be found in the following references: $α_2$-antiplasmin precursor [M.

Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984)).

peptides which are substrates or inhibitors of angiotensin, such as: angiotensin II Asp-Arg-Val-Tyr-Ile-His-Pro-Phe (E. C. Jorgensen et al, *J. Med. Chem.*, 1979, Vol 22, 9, 1038-1044)

[Sar, Ile] Angiotensin II: Sar-Arg-Val-Tyr-Ile-His-Pro-Ile (R. K. Turker et al., *Science,* 1972, 177, 1203).

Angiotensin I: Asp-Arg-Val-Tyr-Ile-His-Pro-Phe-His-Leu.

Preferably the peptides of the present invention comprise RGD or angiotensin II peptides. Synthetic peptides of the present invention may be obtained by conventional solid phase synthesis, as described in P. Lloyd-Williams, F. Albericio and E. Girald; *Chemical Approaches to the Synthesis of Peptides and Proteins*, CRC Press, 1997.

Suitable monoclonal antibodies or fragments thereof for use in the present invention include: antibodies to the CD-20 antigen expressed on the surface of B-cells; anti-leucocyte or anti-granulocyte antibodies; anti-myosin antibodies or antibodies to carcinoembryonic antigen (CEA).

Suitable enzyme substrates, antagonists or inhibitors include glucose and glucose analogues such as fluorodeoxyglucose; fatty acids, or elastase, Angiotensin II or metalloproteinase inhibitors. A preferred non-peptide Angiotensin II antagonist is Losartan.

Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor.

The biological targeting moiety is preferably of molecular weight of less than 5000, most preferably less than 4000, ideally less than 3000.

The "radioisotope suitable for medical imaging" may be detected either external to the mammalian body or via use of detectors designed for use in vivo, such as intravascular radiation or radiation detectors designed for intra-operative use. Preferred such radioisotopes are those which can be detected externally in a non-invasive manner following administration in vivo. Most preferred such radioisotopes are chosen from: radioactive metal ions, gamma-emitting radioactive halogens and positron-emitting radioactive non-metals, particularly those suitable for imaging using SPECT or PET.

When the radioisotope is a radioactive metal ion, ie. a radiometal, suitable radiometals can be either positron emitters such as $^{64}$Cu, $^{48}$V, $^{52}$Fe, $^{55}$Co, $^{98m}$Tc or $^{68}$Ga; γ-emitters such as $^{99m}$Tc, $^{111}$In, $^{113m}$In, or $^{67}$Ga. Preferred radiometals are $^{99m}$Tc, $^{64}$Cu, $^{68}$Ga and $^{111}$In. Most preferred radiometals are γ-emitters, especially $^{99m}$Tc.

When the radioisotope is a gamma-emitting radioactive halogen, the radiohalogen is suitably chosen from $^{123}$I, $^{131}$I or $^{77}$Br. A preferred gamma-emitting radioactive halogen is $^{123}$I.

When the radioisotope is a positron-emitting radioactive non-metal, suitable such positron emitters include: $^{11}$C, $^{13}$N, $^{15}$O, $^{17}$F, $^{18}$F, $^{75}$Br, $^{76}$Br or $^{124}$I. Preferred positron-emitting radioactive non-metals are $^{11}$C, $^{13}$N, $^{18}$F and $^{124}$I, especially $^{11}$C and $^{18}$F, most especially $^{18}$F.

When the radioisotope is a radioactive metal ion, the radiopharmaceutical preferably comprises a metal complex of the radioactive metal ion with a synthetic ligand. By the term "metal complex" is meant a coordination complex of the metal ion with one or more ligands. The term 'synthetic ligand' as used herein means a carbon-containing compound which comprises at least one heteroatom suitable for coordination to a metal, such as N, O, S, P or Se, or combinations thereof. Such compounds have the advantage that their manufacture and impurity profile can be fully controlled.

It is strongly preferred that the metal complex is "resistant to transchelation", ie. does not readily undergo ligand exchange with other potentially competing ligands for the metal coordination sites. Potentially competing ligands include other excipients in the preparation in vitro (eg. radioprotectants or antimicrobial preservatives used in the preparation), or endogenous compounds in vivo (eg. glutathione, transferrin or plasma proteins). The term "synthetic" has its conventional meaning, ie. man-made as opposed to being isolated from natural sources eg. from the mammalian body.

Preferred synthetic ligands for use in the present invention which form metal complexes resistant to transchelation include: chelating agents, where 2-6, preferably 2-4, metal donor atoms are arranged such that 5- or 6-membered chelate rings result (by having a non-coordinating backbone of either carbon atoms or non-coordinating heteroatoms linking the metal donor atoms) upon coordination; or monodentate ligands which comprise donor atoms which bind strongly to the metal ion, such as isonitriles, phosphines or diazenides. The synthetic ligand of the present invention preferably comprises one or more phosphine, thiol or isonitrile metal-binding groups.

Examples of donor atom types which bind well to metals as part of chelating agents are: amines, thiols, amides, oximes and phosphines. Phosphines form such strong metal complexes that even monodentate or bidentate phosphines form suitable metal complexes. The linear geometry of isonitriles and diazenides is such that they do not lend themselves readily to incorporation into chelating agents, and are hence typically used as monodentate ligands. Examples of suitable isonitriles include simple alkyl isonitriles such as tert-butylisonitrile, and ether-substituted isonitriles such as mibi (i.e. 1-isocyano-2-methoxy-2-methylpropane). Examples of preferred phosphines include Tetrofosmin, and monodentate phosphines such as tris(3-methoxypropyl)phosphine. Tetrofosmin is an especially preferred phosphine.

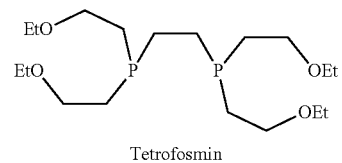 [SMILES: CCOCCP(CCOCC)CCP(CCOCC)CCOCC]

Tetrofosmin

Tetrofosmin can be prepared as described by Chen et al [Zhong. Heyix. Zazhi, 17(1) 13-15 (1997)] or Reid et al [Synth. Appl. Isotop. Lab. Comp., Vol 7, 252-255 (2000)]. The usual synthesis involves first preparing 1,2-bis(phosphino)ethane or H$_2$PCH$_2$CH$_2$PH$_2$ [Inorganic Synthesis, Vol 14, 10], followed by free radical addition of excess ethyl vinyl ether using a free radical initiator.

Examples of suitable diazenides include the HYNIC series of ligands i.e. hydrazine-substituted pyridines or nicotinamides.

Examples of suitable chelating agents for technetium which form metal complexes resistant to transchelation include, but are not limited to:
(i) diaminedioximes of formula:

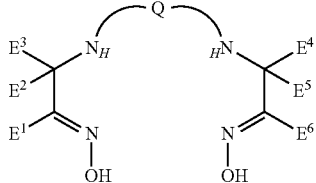

where $E^1$-$E^6$ are each independently an R' group;
each R' is H or $C_{1-10}$ alkyl, $C_{3-10}$ alkylaryl, $C_{2-10}$ alkoxyalkyl, $C_{1-10}$ hydroxyalkyl, $C_{1-10}$ fluoroalkyl, $C_{2-10}$ carboxyalkyl or $C_{1-10}$ aminoalkyl, or two or more R' groups together with the atoms to which they are attached form a carbocyclic, heterocyclic, saturated or unsaturated ring, and wherein one or more of the R' groups is conjugated to the biological targeting molecule;
and Q is a bridging group of formula -(J)$_f$-;
where f is 3, 4 or 5 and each J is independently —O—, —NR'— or —C(R')$_2$— provided that -(J)$_f$-contains a maximum of one J group which is —O— or —NR'—.
Preferred Q groups are as follows:
Q=—(CH$_2$)(CHR')(CH$_2$)— ie. propyleneamine oxime or PnAO derivatives;
Q=—(CH$_2$)$_2$(CHR')(CH$_2$)$_2$— ie. pentyleneamine oxime or PentAO derivatives;
Q=—(CH$_2$)$_2$NR'(CH$_2$)$_2$—.
$E^1$ to $E^6$ are preferably chosen from: $C_{1-3}$ alkyl, alkylaryl alkoxyalkyl, hydroxyalkyl, fluoroalkyl, carboxyalkyl or aminoalkyl. Most preferably, each $E^1$ to $E^6$ group is CH$_3$.

The targeting molecule is preferably conjugated at either the $E^1$ or $E^6$ R' group, or an R' group of the Q moiety. Most preferably, the targeting molecule is conjugated to an R' group of the Q moiety. When the targeting molecule is conjugated to an R' group of the Q moiety, the R' group is preferably at the bridgehead position. In that case, Q is preferably —(CH$_2$)(CHR')(CH$_2$)—, —(CH$_2$)$_2$(CHR')(CH$_2$)$_2$— or —(CH$_2$)$_2$NR'(CH$_2$)$_2$—, most preferably —(CH$_2$)$_2$(CHR')(CH$_2$)$_2$—. An especially preferred bifunctional diaminedioxime chelator has the Formula:

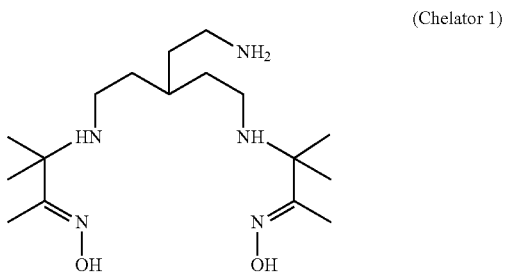 [SMILES: C/C(=N\O)C(C)(C)NCCC(CCN)CCNC(C)(C)/C(C)=N/O]

(Chelator 1)

such that the targeting molecule is conjugated via the bridgehead —CH$_2$CH$_2$NH$_2$ group.
(ii) N$_3$S ligands having a thioltriamide donor set such as MAG$_3$ (mercaptoacetyltriglycine) and related ligands; or having a diamidepyridinethiol donor set such as Pica;
(iii) N$_2$S$_2$ ligands having a diaminedithiol donor set such as BAT or ECD (i.e. ethylcysteinate dimer), or an amideaminedithiol donor set such as MAMA;
(iv) N$_4$ ligands which are open chain or macrocyclic ligands having a tetramine, amidetriamine or diamidediamine donor set, such as cyclam, monoxocyclam or dioxocyclam.
(v) N$_2$O$_2$ ligands having a diaminediphenol donor set.

The above described ligands are particularly suitable for complexing technetium eg. $^{94m}$Tc or $^{99m}$Tc, and are described more fully by Jurisson et al [Chem. Rev., 99, 2205-2218 (1999)]. The ligands are also useful for other radiometals, such as copper ($^{64}$Cu or $^{67}$Cu), vanadium (eg. $^{48}$V), iron (eg. $^{52}$Fe), or cobalt (eg. $^{55}$Co). Other suitable ligands are described in Sandoz WO 91/01144, which includes ligands which are particularly suitable for indium, yttrium and gadolinium, especially macrocyclic aminocarboxylate and aminophosphonic acid ligands. When the radiometal ion is technetium, the ligand is preferably a chelating agent which is tetradentate. Preferred chelating agents for technetium are the diaminedioximes, or those having an N$_2$S$_2$ or N$_3$S donor set as described above.

The "biocompatible carrier" is a fluid, especially a liquid, in which the radiopharmaceutical can be suspended or dissolved, such that the composition is physiologically tolerable, ie. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). Preferably the biocompatible carrier is pyrogen-free water for injection or isotonic saline.

The closure of the present invention seals the container, wherein the integrity of the seal is such that the purity and sterile integrity of the radiopharmaceutical composition is maintained. Seal integrity also means that headspace gas over the radiopharmaceutical composition within the container is maintained, and also that the seal can withstand pressure differentials, such as the application of vacuum during lyophilisation procedures to freeze-dry the container contents. Seal integrity also means that the sterile integrity of the product is maintained during manufacture, transport and clinical use.

The closures of the present invention are suitable for single puncturing with a hypodermic needle (e.g. a crimped-on septum seal closure) whilst maintaining seal integrity. This means that the closure has sufficient elasticity to reform the necessary seal after the puncture hole has been made. For a single puncture, the container may be designed to contain a single human dose, or "unit dose" of the radiopharmaceutical. Preferably, the closures are suitable for multiple puncturing with a hypodermic needle such that the container may have multiple radiopharmaceutical doses therein. Each unit dose withdrawn from the container is for an individual patient, and hence is suitably drawn into a clinical grade syringe for subsequent administration. Preferably the syringe suitable for clinical is disposable, so that the risk of cross-contamination between patients is minimised. The filled syringe may optionally be provided with a syringe shield to protect the operator from radioactive dose. Suitable such radiopharmaceutical syringe shields are known in the art and preferably comprise either lead or tungsten.

The closure of the present invention, ie. the closure body as distinct from the coating thereon, is preferably made of a synthetic, elastomeric polymer. The closure body is preferably made of chlorinated or brominated butyl rubber, or neoprene, since such polymers have low oxygen permeability. The closure body is most preferably made of chlorinated butyl rubber. The radiation resistance depends on the composition of the elastomeric polymer. Radiation resistance is relevant for use with radiopharmaceutical compositions, but also for the possibility of sterilisation of the closures by gamma-irradiation. The present inventors believe that butyl polymers can withstand a radiation dose of around 50 kGy. PTFE can withstand only 5 kGy, which means that PTFE films are not suitable for gamma irradiation. The ETFE film of the present invention can withstand 25-36 kGy, which makes it particularly suitable for the present invention, because gamma-irradiation is a preferred method of sterilisation.

The closures of the present invention are coated on those of its surface(s) which are in contact with the container contents with a coating comprising ethylene-tetrafluoroethylene copolymer (ETFE) or modified versions thereof. The "modified versions" are those commercialised by Dalkyo Seiko as Fluorotec™. The coating is preferably a film which is laminated onto the closure. The thickness of the ETFE film used for laminating the surface of the stopper is preferably in the range 0.01-0.2 mm. If the thickness of the film is less than 0.01 mm, the film tends to break during moulding or processing, whilst if its thickness is greater than 0.2 mm the rigidity of the laminate is too great to maintain proper self-sealing and needle piercing properties.

A preferred ETFE coating is the modified ETFE coating Fluorotec™. Preferably, the coating covers all surfaces of the closure except those which form the sealing area with the container. The "sealing area" is that part of the closure which contacts the container walls (eg. the glass of a vial), and is responsible for providing the air-tight seal. For a vial closure, this means that the coating is not applied on the bottom side of the flange as this area is used for achieving an effective seal between the stopper and vial interface. FIG. 1 shows the sealing area for a commercially available Fluorotec™-coated vial closure. The absence of fluorinated polymer coating on the seal area is important, because the reduced friction of the coating means that fully-coated closures exhibit inadequate seal integrity. This leads to problems with ingress of air into the vial headspace gas as well as difficulties with the application of vacuum (eg. lyophilisation conditions).

Preferred closures of the present invention have a single vent igloo shape. This shape is particularly advantageous for lyophilised products, especially where water/air needs to be removed from the vial (sometimes with backfill of nitrogen) in the freeze-drier apparatus prior to closing the vial. The single vent igloo shape does not have sharp or straight edges and this makes it more suitable for lamination compared to two-legged stoppers, where the edges are very straight and any coating could break during lamination.

The ETFE coating also provides an excellent barrier against potential organic and inorganic extractables to minimize interaction between the drug product and the closure. The fluorocarbon film also has a low surface energy, conferring good lubricity without the need for silicon oil, eliminating one source of particulate contamination. The film also ensures that the stoppers do not stick to the shelves in lyophilisation chambers or clump together during batch production procedures.

It is preferred that the closures of the present invention are pre-treated to remove oxygen gas dissolved within the closure material and/or coating, and the closures re-equilibrated under an atmosphere of a chemically unreactive gas, as defined above, preferably nitrogen or argon. This can be carried out by a variety of methods including:

(i) dry heat to expel the air/oxygen followed by cooling in the presence of the unreactive gas;
(ii) application of high vacuum (eg. in a freeze-drier apparatus) followed by introducing the unreactive gas;
(iii) combinations of (i) and (ii).

Such pre-treatment has been found to be particularly useful for air-sensitive radiopharmaceuticals, since it means that the oxygen content in the headspace gas of the container can be maintained at a very low and stable level. The rationale is that the ETFE coating and/or the closure body rubber formulation is able to absorb oxygen and that small amount of oxygen gas could be released slowly into the vial on storage. Oxygen gas is believed to be highly soluble in the ETFE film coating and the gas would be released into the vial via a diffusion process. This process would be accelerated whenever the pressure inside the container is less than atmospheric pressure (which is sometimes the case with lyophilised agents). A preferred such pre-treatment method is method (i), ie. dry heat.

Air-sensitive radiopharmaceutical agents are as described above. A preferred such agent for the present invention is $^{99m}$Tc-tetrofosmin.

Suitable closures for use in the present invention are commercially available from West Pharmaceutical Services Inc. (www.westpharma.com, 101 Gordon Drive, PO Box 645 Lionville, Pa. 19341, USA) or Dalkyo Seiko Ltd (38-2 Sumida 3-Chome, Sumida-Ku, Tokyo, 131-0031, Japan) and have the modified ETFE coating Fluorotec™. A preferred closure is the D21 series from Dalkyo Seiko. A preferred vial closure from that series has the configuration V10 F451 W, and chlorobutyl rubber formulation denoted D21-7S. This corresponds to Closure 5 of Example 1 (below). The partially-coated closures of the present invention are prepared by a two-step moulding process. First the plug is moulded, trimmed and washed and then applied to the flange. This technique is very different from spray coating where the whole surface area of the closure is coated.

Preferred radiopharmaceuticals for use in the products of the present invention are those which are air-sensitive, or prone to closure adsorption or interaction problems eg. by virtue of lipophilicity having an octanol-water partition coefficient greater than 0.5.

When the radiopharmaceutical comprises a metal complex of a radioactive metal with a synthetic ligand, preferred synthetic ligands are those which comprise phosphine, thiol or isonitrile metal-binding groups. When the radioisotope is $^{99m}$Tc or $^{95m}$Tc, preferred metal-binding groups comprise: Tetrofosmin; MIBI (1-isocyano-2-methoxy-2-methylpropane); BAT (bis aminothiol $N_2S_2$ chelator) or MAG3 ($N_3S$ mercaptoacetyltriglycine). An especially preferred radiopharmaceutical for use in the products of the present invention is $^{99m}$Tc-tetrofosmin in the Tc(V) oxidation state, ie. $^{99m}$Tc(O)$_2$(tetrofosmin)$_2^+$ (Myoview™). $^{99m}$Tc-tetrofosmin has been reported to suffer from plastic adsorption problems [Rodrigues et al., Nucl. Med. Comm., 22(1) 105-110 (2001)]; and Gunasekera et al., Nucl. Med. Comm., 22(5) 493-497 (2001)], so is expected to benefit from reduction or elimination of the possibility of closure interaction problems resulting in eg. the loss of radioactivity.

When the radioisotope is a positron emitter, preferably $^{18}$F, the sealed container of the first embodiment is preferably used as part of an automated synthesizer. By the term "automated synthesizer" is meant an automated module based on the principle of unit operations as described by Satyamurthy et al [Clin. Positr. Imag., 2(5), 233-253

(1999)]. The term 'unit operations' means that complex processes are reduced to a series of simple operations or reactions, which can be applied to a range of materials. Such automated synthesizers are preferred for the method of the third aspect (below), and are commercially available from a range of suppliers [Satyamurthy et al, above], including CTI Inc, GE Healthcare and Ion Beam Applications S.A. (Chemin du Cyclotron 3, B-1348 Louvain-La-Neuve, Belgium). Commercial automated synthesizers also designed to either provide suitable radiation shielding, or to be unshielded but located in a shielded hot cell (ie. a manufacturing cell specially designed for carrying out radiochemistry) to protect the operator from potential radiation dose. Such commercial synthesizers also comprise suitable containers for the liquid radioactive waste generated as a result of the radiopharmaceutical preparation.

Preferred automated synthesizers are those which comprise a disposable or single use cassette which comprises all the non-radioactive reagents, reaction vessels and apparatus necessary to carry out the preparation of a given batch of radiopharmaceutical. The cassette means that the automated synthesizer has the flexibility to be capable of making a variety of different radiopharmaceuticals with minimal risk of cross-contamination, by simply changing the cassette. By the term "cassette" is meant a piece of apparatus designed to fit removably and interchangeably onto an automated synthesizer apparatus (as defined above), in such a way that mechanical movement of moving parts of the synthesizer controls the operation of the cassette from outside the cassette, ie. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

In a second aspect, the present invention provides a kit for the preparation of the imaging agent product of the first embodiment, which comprises the sealed container with closure as defined in the first embodiment, having provided therein a non-radioactive precursor suitable for the preparation of the radiopharmaceutical composition as defined in the first embodiment, wherein said precursor comprises a reactive substituent ($X^R$) capable of reaction with a supply of the radioisotope of in the first embodiment to give said radiopharmaceutical composition.

The radiopharmaceutical of the imaging agent product and preferred aspects thereof are as described for the first embodiment (above).

The "precursor" suitably comprises a non-radioactive derivative designed so that chemical reaction with a convenient chemical form of the desired radioisotope occurs site-specifically; can be conducted in the minimum number of steps (ideally a single step); and without the need for significant purification (ideally no further purification), to give the desired radiopharmaceutical. Such precursors are synthetic and can conveniently be obtained in good chemical purity. The "precursor" may optionally comprise a protecting group ($P^{GP}$) for certain functional groups of any biological targeting molecule present. Suitable precursors described by Bolton, J. Lab. Comp. Radiopharm., 45, 485-528 (2002).

By the term "protecting group" ($P^{GP}$) is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Protecting groups are well known to those skilled in the art and are suitably chosen from, for amine groups: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl); and for carboxyl groups: methyl ester, tert-butyl ester or benzyl ester. For hydroxyl groups, suitable protecting groups are: methyl, ethyl or tert-butyl; alkoxymethyl or alkoxyethyl; benzyl; acetyl; benzoyl; trityl (Trt) or trialkylsilyl such as tert-butyldimethylsilyl. For thiol groups, suitable protecting groups are: trityl and 4-methoxybenzyl. The use of further protecting groups are described in 'Protective Groups in Organic Synthesis', Theorodora W. Greene and Peter G. M. Wuts, (Third Edition, John Wiley & Sons, 1999).

The kits of the second embodiment preferably comprise the precursor in sterile, non-pyrogenic form, so that reaction with a sterile source of the radioisotope gives the desired radiopharmaceutical with the minimum number of manipulations. Such considerations are particularly important for radiopharmaceuticals where the radioisotope has a relatively short half-life, and for ease of handling and hence reduced radiation dose for the radiopharmacist. Hence, the reaction medium for reconstitution of such kits is preferably a "biocompatible carrier" as defined above, and is most preferably aqueous.

The kit sealed containers and preferred embodiments thereof are as described for the first embodiment.

Suitable reactive substituents ($X^R$) comprise:
(i) a synthetic ligand capable of complexing a radioactive metal ion;
(ii) an organometallic derivative such as a trialkylstannane or a trialkylsilane;
(iii) an alkyl halide, alkyl tosylate or alkyl mesylate for nucleophilic substitution;
(iv) a derivative containing an aromatic ring activated towards nucleophilic or electrophilic substitution;
(v) a derivative containing a functional group which undergoes facile alkylation;
(vi) a derivative which alkylates thiol-containing compounds to give a thioether-containing product;
(vii) a derivative which undergoes condensation with an aldehyde or ketone;
(viii) a derivative which is acylated by an active ester group.

When the radioisotope comprises a radioactive metal ion, preferred precursors are those wherein $X^R$ comprises a synthetic ligand. Suitable synthetic ligands, including preferred aspects thereof are as described for the first embodiment. As noted in the first embodiment, the synthetic ligand may optionally be conjugated to a biological targeting molecule.

When the radioisotope comprises a gamma-emitting radioactive halogen or a positron-emitting radioactive non-metal, preferred precursors are those wherein $X^R$ comprises a derivative which either undergoes direct electrophilic or nucleophilic halogenation; undergoes facile alkylation with a labelled alkylating agent chosen from an alkyl or fluoroalkyl halide, tosylate, triflate (ie. trifluoromethanesulphonate), mesylate, maleimide or a labelled N-haloacetyl moiety; alkylates thiol moieties to form thioether linkages; or undergoes condensation with a labelled active ester, aldehyde or ketone. Examples of the first category are:
(a) organometallic derivatives such as a trialkylstannane (eg. trimethylstannyl or tributylstannyl), or a trialkylsilane (eg. trimethylsilyl);
(b) a non-radioactive alkyl iodide or alkyl bromide for halogen exchange and alkyl tosylate, mesylate or triflate for nucleophilic halogenation;
(c) aromatic rings activated towards electrophilic halogenation (eg. phenols) and aromatic rings activated towards nucleophilic halogenation (eg. aryl iodonium, aryl diazonium, aryl trialkylammonium salts or nitroaryl derivatives).

Preferred derivatives which undergo facile alkylation are alcohols, phenols, amine or thiol groups, especially thiols and sterically-unhindered primary or secondary amines. Preferred derivatives which alkylate thiol-containing radioisotope reactants are maleimide derivatives or N-haloacetyl groups. Preferred examples of the latter are N-chloroacetyl and N-bromoacetyl derivatives.

Preferred derivatives which undergo condensation with a labelled active ester moiety are amines, especially sterically-unhindered primary or secondary amines.

Preferred derivatives which undergo condensation with a labelled aldehyde or ketone are aminooxy and hydrazides groups, especially aminooxy derivatives.

The "precursor" may optionally be supplied covalently attached to a solid support matrix. In that way, the desired imaging agent product forms in solution, whereas starting materials and impurities remain bound to the solid phase. Precursors for solid phase electrophilic fluorination with $^{18}$F-fluoride are described in WO 03/002489. Precursors for solid phase nucleophilic fluorination with $^{18}$F-fluoride are described in WO 03/002157. The solid support-bound precursor may therefore be provided as a kit cartridge which can be plugged into a suitably adapted automated synthesizer. The cartridge may contain, apart from the solid support-bound precursor, a column to remove unwanted fluoride ion, and an appropriate vessel connected so as to allow the reaction mixture to be evaporated and allow the product to be formulated as required. The reagents and solvents and other consumables required for the synthesis may also be included together with a compact disc carrying the software which allows the synthesiser to be operated in a way so as to meet the customer requirements for radioactive concentration, volumes, time of delivery etc. Conveniently, all components of the kit are disposable to minimise the possibility of contamination between runs and will be sterile and quality assured.

When the radioisotope is a radiohalogen, $X^R$ suitably comprises: a non-radioactive precursor halogen atom such as an aryl iodide or bromide (to permit radioiodine exchange); an activated precursor aryl ring (e.g. phenol or aniline groups); an imidazole ring; an indole ring; an organometallic precursor compound (eg. trialkyltin or trialkylsilyl); or an organic precursor such as triazenes or a good leaving group for nucleophilic substitution such as an iodonium salt.

Methods of introducing radioactive halogens (including $^{123}$I and $^{18}$F) are described by Bolton [J. Lab. Comp. Radiopharm., 45, 485-528 (2002)]. Examples of suitable precursor aryl groups to which radioactive halogens, especially iodine can be attached are given below:

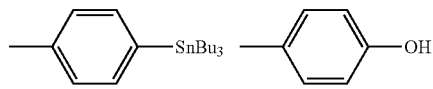

Both contain substituents which permit facile radioiodine substitution onto the aromatic ring. Alternative substituents containing radioactive iodine can be synthesised by direct iodination via radiohalogen exchange, e.g.

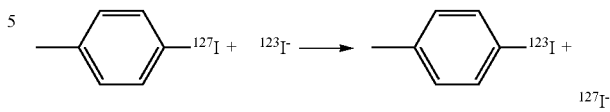

When the radiohalogen comprises a radioactive isotope of iodine, the radioiodine atom is preferably attached via a direct covalent bond to an aromatic ring such as a benzene ring, or a vinyl group since it is known that iodine atoms bound to saturated aliphatic systems are prone to in vivo metabolism and hence loss of the radioiodine. An iodine atom bound to an activated aryl ring like phenol has also, under certain circumstances, been observed to have limited in vivo stability.

When the radioisotope comprises a radioactive halogen, such as $^{123}$I or $^{18}$F, $X^R$ preferably comprises a functional group that will react selectively with a radiolabelled synthon and thus upon conjugation gives the radiopharmaceutical. By the term "radiolabelled synthon" is meant a small, synthetic organic molecule which is:
(i) already radiolabelled such that the radiolabel is bound to the synthon in a stable manner;
(ii) comprises a functional group designed to react selectively and specifically with a corresponding functional group which is part of the desired compound to be radiolabelled. This approach gives better opportunities to generate radiopharmaceuticals with improved in vivo stability of the radiolabel relative to direct radiolabelling approaches.

A synthon approach also allows greater flexibility in the conditions used for the introduction of the radioisotope. This is important when eg. the biological targeting molecule exhibits significant instability under basic conditions. In addition, they are therefore not suitable for conventional direct labelling approaches via nucleophilic displacement reactions under basic conditions.

Examples of precursors suitable for the generation of imaging agents of the present invention are those where $X^R$ comprises an aminooxy group, a thiol group, an amine group, a maleimide group or an N-haloacetyl group. A preferred method for selective labelling is to employ aminooxy derivatives of peptides as precursors, as taught by Poethko et al [J. Nuc. Med., 45, 892-902 (2004)]. Such precursors are then condensed with a radiohalogenated-benzaldehyde synthon under acidic conditions (eg. pH 2 to 4), to give the desired radiohalogenated agent via a stable oxime ether linkage. $X^R$ therefore preferably comprises an aminooxy group of formula —NH(C=O)CH$_2$—O—NH$_2$. Another preferred method of labelling is when $X^R$ comprises a thiol group which is alkylated with radiohalogenated maleimide-containing synthon under neutral conditions (pH 6.5-7.5) eg. as taught by Toyokuni et al [Bioconj. Chem. 14, 1253-1259 (2003)] to label thiol-containing peptides.

An additional preferred method of labelling is when $X^R$ comprises an amine group which is condensed with the synthon N-succinimidyl 4-[$^{123}$I]iodobenzoate at pH 7.5-8.5 to give amide bond linked products. The use of N-hydroxysuccinimide ester to label peptides is taught by Vaidyanathan et al [Nucl. Med. Biol., 19(3), 275-281 (1992)] and Johnstrom et al [Clin. Sci., 103 (Suppl. 48), 45-85 (2002)].

When the radioisotope comprises a radioactive isotope of fluorine, the radiofluorine atom may form part of a fluoroalkyl or fluoroalkoxy group, since alkyl fluorides are resistant to in vivo metabolism. The radiofluorination may be carried out via direct labelling using the reaction of $^{18}$F-fluoride with a suitable precursor having a good leaving group, such as an alkyl bromide, alkyl mesylate or alkyl tosylate. Alternatively, the radiofluorine atom may be attached via a direct covalent bond to an aromatic ring such as a benzene ring. For such aryl systems, the precursor suitably comprises an activated nitroaryl ring, an aryl diazonium salt, or an aryl trialkylammonium salt. The direct radiofluorination of biomolecules is, however, often detrimental to sensitive functional groups since these nucleophilic reactions are carried out with anhydrous [$^{18}$F]fluoride ion in polar aprotic solvents under strong basic conditions.

When the precursor of the second embodiment is unstable under basic conditions, direct radiofluorination of precursors is not a preferred labelling method. In such circumstances, preferred methods for radiofluorination involve the use of radiolabelled synthons that are conjugated selectively to the precursor, as discussed above for the labelling with radiohalogens in general.

$^{18}$F can also be introduced by N-alkylation of amine precursors with alkylating agents such as $^{18}$F(CH$_2$)$_3$OMs (where Ms is mesylate) to give N—(CH$_2$)$_3$$^{18}$F, O-alkylation of hydroxyl groups with $^{18}$F(CH$_2$)$_3$OMs, $^{18}$F(CH$_2$)$_3$OTs or $^{18}$F(CH$_2$)$_3$Br or S-alkylation of thiol groups with $^{18}$F(CH$_2$)$_3$OMs or $^{18}$F(CH$_2$)$_3$Br. $^{18}$F can also be introduced by alkylation of N-haloacetyl groups with a $^{18}$F(CH$_2$)$_3$OH reactant, to give —NH(CO)CH$_2$O(CH$_2$)$_3$$^{18}$F derivatives or with a $^{18}$F(CH$_2$)$_3$SH reactant, to give —NH(CO)CH$_2$S(CH$_2$)$_3$$^{18}$F derivatives. $^{18}$F can also be introduced by reaction of maleimide-containing precursors with $^{18}$F(CH$_2$)$_3$SH. For aryl systems, $^{18}$F-fluoride nucleophilic displacement from an aryl diazonium salt, an aryl nitro compound or an aryl quaternary ammonium salt are suitable routes to aryl-18F labelled synthons useful for conjugation to precursors.

Precursors where X$^R$ comprises a primary amine group can also be labelled with $^{18}$F by reductive amination using $^{18}$F—C$_6$H$_4$—CHO as taught by Kahn et al [J. Lab. Comp. Radiopharm. 45, 1045-1053 (2002)] and Borch et al [J. Am. Chem. Soc. 93, 2897 (1971)]. This approach can also usefully be applied to aryl primary amines, such as compounds comprising phenyl-NH$_2$ or phenyl-CH$_2$NH$_2$ groups.

An especially preferred method for $^{18}$F-labelling of peptide-based precursors is when X$^R$ comprises an aminooxy group of formula —NH(C=O)CH$_2$—O—NH$_2$ which is condensed with $^{18}$F—C$_6$H$_4$—CHO under acidic conditions (eg. pH 2 to 4). This method is particularly useful for precursors which are base-sensitive.

Further details of synthetic routes to $^{18}$F-labelled derivatives are described by Bolton, J. Lab. Comp. Radiopharm., 45, 485-528 (2002).

The non-radioactive kits of the second embodiment may optionally further comprise additional components such as a radioprotectant, antimicrobial preservative, pH-adjusting agent or filler.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (ie. 4-aminobenzoic acid), gentisic acid (ie. 2,5-dihydroxybenzoic acid) and salts thereof with a biocompatible cation. By the term "biocompatible cation" is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the radiopharmaceutical composition post-reconstitution, ie. in the radioactive diagnostic product itself. The antimicrobial preservative may, however, also optionally be used to inhibit the growth of potentially harmful micro-organisms in one or more components of the non-radioactive kit of the present invention prior to reconstitution. Suitable antimicrobial preservative(s) include: the parabens, ie. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the reconstituted kit is within acceptable limits (approximately pH 4.0 to 10.5) for human or mammalian administration. Suitable such pH-adjusting agents include pharmaceutically acceptable buffers, such as tricine, phosphate or TRIS [ie. tris(hydroxymethyl)aminomethane], and pharmaceutically acceptable bases such as sodium carbonate, sodium bicarbonate or mixtures thereof. When the conjugate is employed in acid salt form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

Preferred kits of the present invention are those which comprise the preferred precursors described above for each class of radioisotope, ie. radioactive metal ions, gamma-emitting radiohalogens or positron-emitting radioactive non-metals.

The kits of the present invention are particularly useful for precursors which are lyophilised and designed to give sterile, pyrogen-free preparations. Such kits may need to have a useful shelf-life of several months, and hence any air-sensitivity or adsorption problems are likely to be exacerbated. When the kit is for the preparation of a radiopharmaceutical which comprises a metal complex of a radioactive metal with a synthetic ligand, preferred synthetic ligand precursors are those which comprise phosphine, thiol or isonitrile metal-binding groups. When the radioisotope is $^{99m}$Tc or $^{95m}$Tc, preferred metal-binding groups comprise: Tetrofosmin; MIBI (1-isocyano-2-methoxy-2-methylpropane); BAT (bis aminothiol N$_2$S$_2$ chelator) such as the tropane chelator conjugate TRODAT-1 [Meegalla et al, J. Med. Chem., 40, 9-17 (1997)]; or MAG3 (N$_3$S mercaptoacetyltriglycine). An especially preferred metal-binding group is Tetrofosmin.

The kit of the second embodiment may optionally be formulated as a multi-dose kit, wherein the kit is formulated such that 4 to 30 unit patient doses of the radiopharmaceutical can be obtained from a single kit. The multi-dose kit has to be sufficiently robust to withstand significantly higher levels of radioactivity, and also greater volumes of solution than the conventional kit. Containers for the multi-dose vial are suitably of 20 to 50 cm$^3$ volume, preferably 20 to 40 cm$^3$, most preferably 30 cm$^3$ volume. The multi-dose kit comprises sufficient material for multiple patient doses (eg. up to 100 GBq of $^{99m}$Tc per vial), whereby unit patient doses can thus be withdrawn into clinical grade syringes at various time intervals during the viable lifetime of the stabilised preparation to suit the clinical situation. The multi-dose kits of the present invention are formulated to be suitable for obtaining 4 to 30, preferably 6 to 24 such unit doses of radiopharmaceutical in a reproducible manner.

By definition, such multi-dose kits need to able to withstand significant numbers of closure punctures whilst maintaining sterile integrity, and without generation of unwanted closure particulates ("coring"), which might loosen and fall into the radiopharmaceutical composition. The closures of the present invention have been shown to be capable of withstanding such multiple puncturing successfully.

An especially preferred synthetic ligand precursor for use in the kits of the present invention is tetrofosmin. An especially preferred tetrofosmin kit formulation corresponds to that of the GE Healthcare heart imaging agent Myoview™, ie. the lyophilised formulation:

| Tetrofosmin | 0.23 mg |
|---|---|
| Stannous chloride dihydrate | 30 μg |
| Disodium sulfosalicylate | 0.32 mg |
| Sodium-D-gluconate | 1.0 mg |
| Sodium hydrogen carbonate | 1.8 mg |
| pH on reconstitution | 8.3-9.1, | which is sealed under nitrogen gas USP/NF in a 10 ml glass vial, which upon reconstitution with Sterile Sodium ($^{99m}$Tc) Pertechnetate Injection USP/Ph. Eur., yields a solution containing the heart imaging radiopharmaceutical $^{99m}$Tc-tetrofosmin.

The tetrofosmin kit may optionally comprise a radioprotectant, as defined above. The incorporation of an ascorbic acid radioprotectant in such kits has been found to confer the advantage that the $^{99m}$Tc-tetrofosmin complex is prepared in good radiochemical purity (RCP) and with good post-reconstitution stability for up to 12 hours post preparation, without the need for the air addition step taught by both the prior art [Murray et al, Nucl. Med. Comm., 21, 845-849 (2000)] and the Myoview™ Package Instructions. This is a useful simplification, since it removes a process step which means one less manipulation and hence results in reduced radiation dose for the operator, as well as being quicker and easier to carry out. The air addition step is also somewhat unusual in radiopharmacy practice and hence there is a risk that it might inadvertently be omitted, with consequent adverse effect on RCP.

The concentration of radioprotectant for use in tetrofosmin-containing kits of the present invention is suitably 0.0003 to 0.7 molar, preferably 0.001 to 0.07 molar, most preferably 0.0025 to 0.01 molar. For ascorbic acid, this corresponds to a suitable concentration of 0.05 to 100 mg/cm$^3$, preferably 0.2 to 10 mg/cm$^3$, most preferably 0.4 to 1.5 mg/cm$^3$.

The tetrofosmin-containing kit of the present invention is preferably formulated such that the pH of the solution on reconstitution with water or saline is 8.0 to 9.2, most preferably 8.0 to 8.6. This means that, when the radioprotectant is ascorbic acid, ie. an acid, the amount of pH adjusting agent needs to be adjusted. This is necessary to ensure that the optimum pH of the kit for: $^{99m}$Tc radiolabelling of tetrofosmin; post-reconstitution stability and suitability for patient administration, are maintained. A preferred such kit formulation for a 30 ml multi-dose vial presentation is:

| Tetrofosmin | 0.69 mg, |
|---|---|
| Stannous chloride dihydrate | 90 μg, |
| Disodium sulfosalicylate | 0.96 mg, |
| Sodium-D-gluconate | 3.0 mg, |
| Ascorbic acid | 5.0 mg, |
| Sodium hydrogen carbonate | 11.0 mg, |
| pH on reconstitution with saline | 8.3 to 9.1. |

The radioprotectants for tetrofosmin-containing kits are preferably chosen from ascorbic acid and salts thereof with a biocompatible cation. The radioprotectants of the present invention are commercially available from a number of suppliers.

Tetrofosmin is a tertiary phosphine, and moderately air-sensitive. Tetrofosmin-containing kits are therefore particularly sensitive to any ingress of oxygen into the headspace gas. The oxidation to the phosphine oxide is essentially irreversible, and impacts on the non-radioactive viable shelf-life of the kit. The present inventors note that the oxygen content of the headspace is not simply a function of closure porosity. Thus, the effectiveness of closure-container seal during the freeze-drying process is also extremely important for lyophilised kits. The closures of the present invention fulfil both criteria, whereas many fluorocarbon-coated closures are not always suitable for lyophilised products. The ETFE coating also helps suppress adsorption of the precursor to the closure, and this has been found to be particularly useful for tetrofosmin.

This leads to significant advantages. First, the useful shelf-life of the non-radioactive kits can be extended from 35 to ca. 52 weeks (when pre-treated closures are used). Secondly, Myoview™ kits are currently transported at 2 to 8° C. to preserve the performance of the kit. This is achieved by packing the kits in ice packs in insulated containers. With the improved closure and pre-treatment process of the present invention, the kits are expected to be sufficiently stable to be shipped at ambient temperature (ca. 25° C.), thus obviating the need for the additional packaging to maintain cooling.

An extensive range of sources of radioisotope for use in conjunction with the precursor are commercially available either as the radioisotope itself or as a radioisotope generator from a range of suppliers. These include: halide ions such as $^{123}$I-iodide or $^{18}$F-fluoride; or radiometal ions such as $^{111}$In-indium chloride or $^{99m}$Tc-pertechnetate. When the radioisotope is technetium, the usual technetium starting material is pertechnetate, i.e. TcO$_4^-$ which is technetium in the Tc(VII) oxidation state. Pertechnetate itself does not readily form metal complexes, hence the preparation of technetium complexes usually requires the addition of a suitable reducing agent such as stannous ion to facilitate complexation by reducing the oxidation state of the technetium to the lower oxidation states, usually Tc(I) to Tc(V). The solvent may be organic or aqueous, or mixtures thereof, and is preferably a biocompatible carrier. The biocompatible carrier and preferred aspects thereof are as described above.

Other radioisotopes are available via standard methods [McQuade et al, Curr. Med. Chem., 12(7), 807-818 (1995); Finn et al in "Principles & Practice of Positron Emission Tomography", R. L. Wahl et al (Eds), Chapter 1 pages 1-15 (2002) and Elliott et al in "Textbook of Radiopharmacy", 3$^{rd}$ edition, C. B. Sampson (Ed), Chapter 2 pages 19-29 (1999)].

In a third aspect, the present invention provides a method of preparation of the imaging agent product of the first embodiment, which comprises reaction of:
(i) the precursor of the second embodiment; with
(ii) a supply of the radioisotope of the first embodiment; either in the sealed container of the first embodiment or in a separate reaction vessel, followed by transfer of the reaction product to the sealed container of the first embodiment.

Preferred aspects of the precursor of reactant (i) of the method are as described in the second embodiment. The source of radioisotope of reactant (ii) of the method is as described for the first and second embodiments (above). Preferably, the method is carried out such that the precursor is supplied as the kit of the second embodiment. The supply of the radioisotope is preferably supplied in a biocompatible carrier, as described in the first embodiment. Preferably, the preparation method is carried out within the sealed container of Claims 1 to 6, so that no transfer step is necessary.

When the radioisotope is a positron emitter, the preparation method (ie. the reaction and/or transfer of reaction product) is carried out using an automated synthesizer apparatus.

Radiopharmaceutical preparations which require heating to prepare the imaging agent product are particularly expected to benefit from use of the closures or kits of the present invention, since heating increases the probability of closure interactions and/or leaching of impurities from the closure.

In a fourth aspect, the present invention provides the use of the closure as defined in the first embodiment to seal containers comprising either:
(i) the radiopharmaceutical composition of the first embodiment; or
(ii) the kit of the second embodiment.

Preferred radiopharmaceuticals and kits are as described in the first and second embodiments respectively. Preferred closures are as defined in the first embodiment. When the radioisotope of the radiopharmaceutical composition is a positron emitter, the container preferably forms part of an automated synthesizer apparatus. Preferred aspects of the automated synthesizer apparatus are as described above. It is believed that that the advantages of use of such closures for radiopharmaceutical applications have not previously been recognised.

The invention is illustrated by the non-limiting Examples detailed below. Example 1 shows that, for tetrofosmin-containing kits, many closures have less than ideal properties, and that the closures of the present invention provide an important improvement. Example 2 shoes how the closures of the present invention can be improved yet further by pre-treatment to remove dissolved oxygen gas and replacement with nitrogen. Example 3 shows that the RCP profile of a lyophilised tetrofosmin-containing kit prepared using a closure of the present invention was identical to that of a reference Myoview™ kit (uncoated stopper). This shows that there are no new radioactive impurities due to the ETFE-coated closure. Example 4 shows that the closure combinations of the present invention are suitable for use with multi-dose radiopharmaceutical vials. Example 5 provides an improved pre-treatment process to minimise oxygen headspace gas levels in sealed vials of the present invention on shelf-life storage. Example 6 shows that the closures of the present invention exhibit advantages for use with lyophilised radiopharmaceutical kits.

FIG. 1 shows the sealing area for a commercially available Fluorotec™-coated vial closure. FIG. 2 shows the oxygen headspace gas results as a function of time of storage post-preparation.

Example 1: Closures for Lyophilised Tetrofosmin-Containing Kits

The following closures were evaluated:

TABLE 1

| Closure[$] | Formulation | Configuration | Shape[*] | Coating | Composition[§] |
|---|---|---|---|---|---|
| 1 | 4432/50 | 1178 | A | No | Chlorobutyl |
| 2 | 4588/40 | 1178 | A | No | Chlorobutyl/isoprene |
| 3 | D777-1 | V10-F451 W | B | Flurotec ™ | IIR |
| 4 | D777-1 | V10-F597 W | B | Flurotec ™ | IIR |
| 5 | D21-7S | V10-F451 W | B | Flurotec ™ | Chlorobutyl |
| 6 | D21-7S | V10-F597 W | B | Flurotec ™ | Chlorobutyl |
| 7 | FM259/0 | V9154 | A | Omniflex Plus ™ | Bromobutyl |
| 8 | FM259/0 | V9172 | B | Omniflex Plus ™ | Bromobutyl |
| 9 | Ph701/40 | F1018 | B | No | Chlorobutyl |
| 10 | 4416/50 | S87T | A | No | Bromobutyl |
| 11 | B0344C | PT23 | A | Elastoshield ™ | Chlorobutyl |
| 12 | B0344C | PT24 | A | Elastoshield ™ | Chlorobutyl |
| 13 | GR02019900 | SL 13619 | | No | Chlorobutyl |
| 14 | 6720GC 5 | C1558 | A | No | Bromobutyl |

[$]Commercial closures obtained from the suppliers: 1, 2, 9 & 10 West Pharma; 3-6 Daikyo; 7 & 8 Helvoet; 11 & 12 Itran-Tomkins; 13 Seal line and 14 Stelmi.
[*]Shape A = Two leg (double vent)
[*]Shape B = Igloo (single vent)
[§]IIR = Isobutylene-isoprene copolymer.

Tetrofosmin kit lyophilised formulations (according to the Myoview™ formulation cited in the second embodiment) were prepared using closures 1-14 of Table 1. The tetrofosmin content, and oxygen headspace gas content were assayed at time intervals post kit preparation. The headspace oxygen content was measured by purging the vial with pure nitrogen and passing the effluent gas through an electrochemical oxygen detector. The integrated signal gives the total oxygen content. The results, in comparison with the current commercial Myoview™ product (which has uncoated chlorobutyl closure West formulation PH701/45 red brown, shape 1178) are summarised in Table 2:

TABLE 2 comparative closure test results.

| Closure | Results |
|---|---|
| 1 | No evidence of reduced losses of tetrofosmin. |
| 2 | No evidence of reduced losses of tetrofosmin. |
| 3 | Failed oxygen spec after 6 weeks on stability at stressed conditions. |
| 4 | Failed oxygen spec after 6 weeks on stability at stressed conditions. |
| 5 | Passed the oxygen spec after 6 weeks on stability at stressed conditions. |
| 6 | Failed oxygen spec after 6 weeks on stability at stressed conditions. |
| 7 | Failed initial oxygen requirements (LT 10 µl) due to popping out of closures. |
| 8 | Failed initial oxygen requirements (LT 10 µl) due to popping out of closures. |
| 9 | Did not reduce the losses of tetrofosmin. Initially too high on oxygen content. |
| 10 | Did not reduce the losses of tetrofosmin. Initially too high on oxygen content. |
| 11 | Failed initial oxygen requirements (LT 10 µl) due to popping out of closures. |
| 12 | Failed initial oxygen requirements (LT 10 µl) due to popping out of closures. |
| 13 | Did not reduce the losses of tetrofosmin. Initially too high on oxygen content. |
| 14 | Did not reduce the losses of tetrofosmin. Initially too high on oxygen content. |

Example 2: Pre-Treatment of Closures

ETFE-coated closures (Closure #5 of Example 1) were pre-treated by heating in a dry heat oven at two different conditions. The conditions were 123° C. at 15 hours and 80° C. at 20 hours. The closures were allowed to cool and were then packed in polyethene bags and sterilised (using gamma irradiation). The stoppers were used to seal empty glass vials within 1 to 2 days (so as to prevent re-adsorption of oxygen gas into the stopper). The oxygen content in headspace gas of the vial was measured at intervals, and found to be at a very low and stable level (below 2 µl up to 11 weeks post-sealing).

Example 3: Suitability of Closure for Radiopharmaceutical Use

The lyophilised kit of Example 1 with Closure #5 was used. The kit was reconstituted with $^{99m}$Tc pertechnetate in saline (8 ml at 1.1 GBq/ml) and incubated for 15 minutes at room temperature. HPLC analyses were then performed over a period of 12 hours to investigate if there were any new and/or different radiochemical peaks in the Myoview 10 ml product made with the new stopper compared to Myoview with the current uncoated stopper. No differences in the amount of peaks or in the peak sizes were observed. The stopper's mechanical properties or physical appearance were unaffected by the reconstitution.

Example 4: Suitability of Closure for Multi-Use Radiopharmaceutical Vials 36 empty vials were fitted with closures from three different batches of Closure #5 of Example 1 (12 vials per batch). Each batch of closures was subjected to the European Pharmacopoeia fragmentation test, involving piercing with a hypodermic needle (external diameter of 0.8 mm) at 4 different puncture sites. All closures passed. In a further experiment, 6 vials fitted with Closure #5 were pierced 35 times with a needle (gauge 21 G). The number of fragments loosened was still within the European Pharmacopoeia requirements.

Example 5: Alternative Pre-Treatment of Closures

ETFE-coated closures (Closure #5 of Example 1) were subjected to a washing and drying process on a Fedegari Autoclave. Following the washing part of the cycle, there was a 2 minute steam injection and a heating phase of 105° C. for 10 minutes. The next part of the cycle was drying under a vacuum of 200 millibar for 10 minutes, during which time the temperature falls from 105° C. to around 60° C. All closures are dry on removal from the autoclave chamber. The closures were used to seal empty glass vials as described in Example 2. The results are shown in FIG. 2.

Example 6: Suitability of Closure for Lyophilised Radiopharmaceutical Kits

Lyophilised Myoview™ 30 ml kit compositions were prepared as described in the second aspect, using Closure #5 of Example 1. 100% visual inspection was carried out on two batches, each of approximately 21,500 vials. Vials were rejected if lyophilisation powder was visible around the closure. The number of vials rejected due to closure defects was significantly lower than a conventional uncoated closure (PH 701/45 red brown) used on Myoview™ 10 ml kit batches. The number of vials rejected using Closure #5 was 73 on the first batch and 103 on the second batch. This represents a reject rate of approximately 0.3 to 0.5%. The reject rate due to stopper failure for the conventional uncoated closure is around 2%.

What is claimed is:

1. An imaging agent product comprising a tetrofosmin composition within a sealed container,
   the sealed container comprising a pharmaceutical grade glass vial and pre-treated closure suitable for puncturing with a hypodermic needle while maintaining seal integrity, the pre-treated closure comprising a chlorinated butyl rubber body which is coated with ethylene-tetrafluoroethylene copolymer (ETFE) on one or more of its surface(s) which are in contact with the container contents, wherein the pre-treatment of the closure removes oxygen gas dissolved within the closure material so that the sealed container exhibits a headspace having an increase in oxygen of less than 2 microliters after 11 weeks post-sealing;
   the tetrofosmin composition comprises a lyophilized, non-radioactive formulation having a pH in the range of 8.0 to 9.2 in the sealed container, the formulation comprising:
   (i) a tetrofosmin precursor,
   (ii) an optional radioprotectant selected from ascorbic acid or a salt thereof with a biocompatible cation;

(iii) a biocompatible reductant that comprises stannous ion; and (iv) an effective amount of a pH-adjusting agent that is sodium bicarbonate, sodium hydrogen carbonate, or a combination thereof;

wherein the tetrofosmin composition is sealed within the sealed container under nitrogen gas with the pre-treated closure such that the sealed container exhibits reduced losses of tetrofosmin relative tetrofosmin compositions sealed within a container having an uncoated rubber body, and wherein upon reconstitution with $^{99m}$Tc the imaging agent the product yields a $^{99m}$Tc-tetrofosmin imaging agent.

2. The imaging agent product of claim 1, where the coating is laminated onto the closure.

3. The imaging agent product of claim 1, where the coating covers all surfaces of the closure except those which form the sealing area with the container.

4. The imaging agent product of claim 1, wherein the closure is pre-treated by heating in a dry oven.

5. The imaging agent product of claim 1, wherein the closure is pre-treated by heating the closure to remove oxygen gas dissolved within the closure material and/or coating and re-equilibrating the closure under an atmosphere of a chemically unreactive gas.

6. The imaging agent product of claim 1, where the closure has a single vent igloo shape.

7. The imaging agent product of claim 1, wherein the tetrofosmin composition consists essentially of about 0.69 mg tetrofosmin, about 90 µg of stannous chloride dihydrate, about 0.96 mg disodium sulfosalicylate, about 3.0 mg sodium D-gluconate, about 5.0 mg ascorbic acid, about 11.0 mg sodium hydrogen carbonate, and a pH on reconstitution of 8.3 to 9.1.

8. A kit for the preparation of an imaging agent comprising the imaging agent product of claim 1 and a sterile sodium $^{99m}$Tc pertechnetate.

* * * * *

UNITED STATES PATENT AND TRADEMARK OFFICE
CERTIFICATE OF CORRECTION

| | |
|---|---|
| PATENT NO. | : 10,328,164 B2 |
| APPLICATION NO. | : 12/305977 |
| DATED | : June 25, 2019 |
| INVENTOR(S) | : Stig Hemstad |

It is certified that error appears in the above-identified patent and that said Letters Patent is hereby corrected as shown below:

On the Title Page

Please add the following:
Item (71) Applicant --GE HEALTHCARE LIMITED--

Signed and Sealed this
Twenty-seventh Day of August, 2019

Andrei Iancu
*Director of the United States Patent and Trademark Office*